United States Patent [19]

Foote

[11] Patent Number: 5,447,056
[45] Date of Patent: Sep. 5, 1995

[54] TONER CONCENTRATION CONTROL SYSTEM FOR LIQUID ELECTROPHOTOGRAPHY

[75] Inventor: Wayne E. Foote, Eagle, Id.

[73] Assignee: Hewlett-Packard Company, Palo Alto, Calif.

[21] Appl. No.: 253,468

[22] Filed: Jun. 3, 1994

[51] Int. Cl.6 ................ G01N 27/07; G03G 15/10
[52] U.S. Cl. ................ 73/61.71; 73/291;
73/304 R; 324/71.1; 324/693; 355/203;
355/246; 118/689
[58] Field of Search .......... 73/61.71, 291, 304 R,
73/304 C; 355/203, 209, 246; 324/71.1, 693,
697; 118/689, 693, 694

[56] References Cited

U.S. PATENT DOCUMENTS

| | | | |
|---|---|---|---|
| 1,532,871 | 4/1925 | Bloch | 73/304 R |
| 3,802,381 | 4/1974 | O'Neill et al. | 118/7 |
| 4,310,238 | 1/1982 | Mochizuki et al. | 355/246 |
| 4,343,548 | 8/1982 | Bares et al. | 355/246 |
| 4,860,924 | 8/1989 | Simms | 222/56 |
| 5,003,352 | 3/1991 | Duchesne et al. | 355/256 |

Primary Examiner—Hezron E. Williams
Assistant Examiner—Michael J. Brock
Attorney, Agent, or Firm—Anthony J. Baca

[57] ABSTRACT

An "L" shaped element having horizontal and vertical sections, is submerged in the liquid toner concentrate such that the horizontal section is totally submerged while the vertical section is submerged proportionally to an amount of the liquid toner concentrate. A voltage source is connected to the "L" shaped element. A second element is placed in close proximity to the horizontal section of the "L" shaped element and is also totally submerged in the liquid toner concentrate. Next, a third element is placed in close proximity to the vertical section of the "L" shaped element. The current flowing from the horizontal section of the "L" shaped element through the liquid toner concentrate to the second element is proportional to the concentration of solid. By measuring the current flowing from the vertical section of the "L" shaped element through the liquid toner concentrate to the third element and dividing by the current in the second plate, the volume of the liquid toner concentrate can easily be calculated.

8 Claims, 3 Drawing Sheets

TONER CONCENTRATION CONTROL SYSTEM FOR LIQUID ELECTROPHOTOGRAPHY

TECHNICAL FIELD

The present invention relates to an arrangement to determine both the toner concentration and the toner volume remaining in the toner reservoir used for liquid electrophotography. This method is applicable to single color as well as multi-color applications.

BACKGROUND OF THE INVENTION

Electrophotographic printing is well known and has been widely refined. Using electrophotographic techniques, images are photoelectrically formed on a photoconductive layer mounted on a conductive base. Liquid or dry developer or toner mixtures may be used to develop a requisite image. Liquid toner dispersions for use in the process are formed by dispersing dyes or pigments in natural or synthetic resin materials in a high dielectric constant carrier liquid.

The photoconductive layer is sensitized by electrically charging whereby electrical charges are uniformly distributed over the surface. The photoconductive layer is then exposed by projecting or alternatively by writing an image over the surface with a laser, LED, or the like. The electrical charges on the photoconductive layer are conducted away from the areas exposed to the light with an electrostatic charge remaining in the imaged area. The charged pigment and or dye particles from the liquid toner dispersion contact and adhere to the image area of the plate. The image is then transferred to the desired substrate such as a sheet of paper.

With liquid electrophotography (LEP), the image development process requires that the toner be delivered to the developer at relatively constant concentration. However, usage of toner solids and toner carrier fluid in an LEP process are independent of each other. Toner solid consumption is proportional to the print coverage on the page and the number of pages printed. Whereas, toner carrier consumption is independent of print coverage and only a function of the number of pages printed. These characteristics result in toner concentration decreasing for above average page coverage and increasing for below average page coverage. Additionally, toner solids will settle out from the toner carrier over time.

By measuring both the volume and concentration, user feedback can always be made available as to the percentage of usable toner remaining. Process parameters can be changed to dynamically compensate for toner concentration changes to enhance print characteristics over varying toner concentration ratios. Toner replenishment methods can also be initialized from the concentration measurement. Thus, there exists a need to monitor both the toner concentration and the toner volume in the toner reservoir.

SUMMARY OF THE INVENTION

In order to accomplish the present invention, there is provided an apparatus for determining a concentration of solid in a liquid toner concentrate and simultaneously measuring the volume of the liquid toner concentrate.

An "L" shaped element having first and second sections, is submerged in the liquid toner concentrate such that the first section is totally submerged while the second section is submerged proportionally to an amount of the liquid toner concentrate. A voltage source is connected to the "L" shaped element. A second element is placed in close proximity to the first section of the "L" shaped element. For the present invention to operate properly, the second element must also be totally submerged in the liquid toner concentrate. Next, a third element is placed in close proximity to the second section of the "L" shaped element. Because of the proximity to the vertical element, the third element is also submerged proportionally to the amount of the liquid toner concentrate.

The current flowing from the first section through the liquid toner concentrate to the second element is proportional to the concentration of solid. By measuring the current flowing from the second section through the liquid toner concentrate to the third element and dividing by the current in the second element, the volume of the liquid toner concentrate can easily be calculated.

BRIEF DESCRIPTION OF THE DRAWINGS

A better understanding of the invention may be had from the consideration of the following detailed description of the preferred embodiment taken in conjunction with the accompanying drawings in which.

DETAILED DESCRIPTION OF THE PREFERRED EMBODIMENTS

Figure 1:
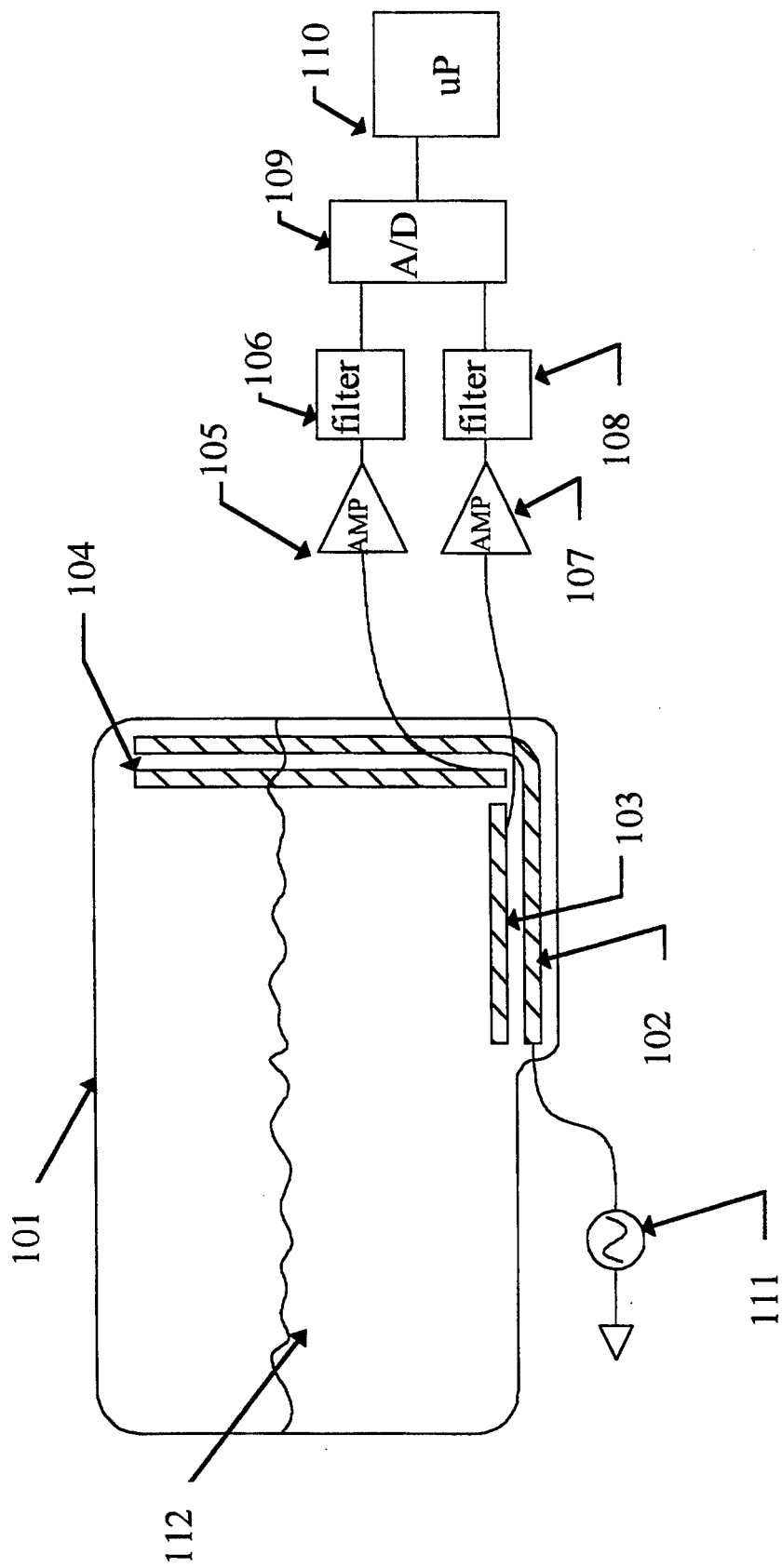
FIG. 1 is a simplified diagram of a preferred embodiment in accordance with the present invention.

The present invention uses the observed physical property that toner conductivity is directly proportional to concentration for the range of interest. Referring first to FIG. 1, the present invention consists of three conductive plates 102, 103, and 104 inserted into a toner reservoir 101. Plate 102 is driven by a low frequency, low voltage sine wave 111. Section 103 is submerged in toner 112 while the third section 104 is submerged proportional to toner 112 volume. Plate 103 is parallel to the always submerged section 102 and is always totally submerged. Plate 104 is parallel to the partially submerged area on the first plate 102 and is submerged proportional to toner volume. With this arrangement, the plate combination of 102 and 103 senses the toner conductivity. Plate combination 104 and 102 determines a total solids remaining from which toner volume is easily calculated.

The current signals from the sensor plates are amplified and converted to a voltage by amplifiers 105 and 107. A pair of filters are used to convert the AC voltage from the amplifiers to a DC value that is fed into a multiplexed analog-to-digital converter (A/D) 109. One skilled on the art will also understand that A/D 109 may not be needed if A/D channels are available in the microprocessor 110. Microprocessor 110, under the direction of its associated software, performs the necessary calculations to determine the toner level and concentration.

Figure 2:
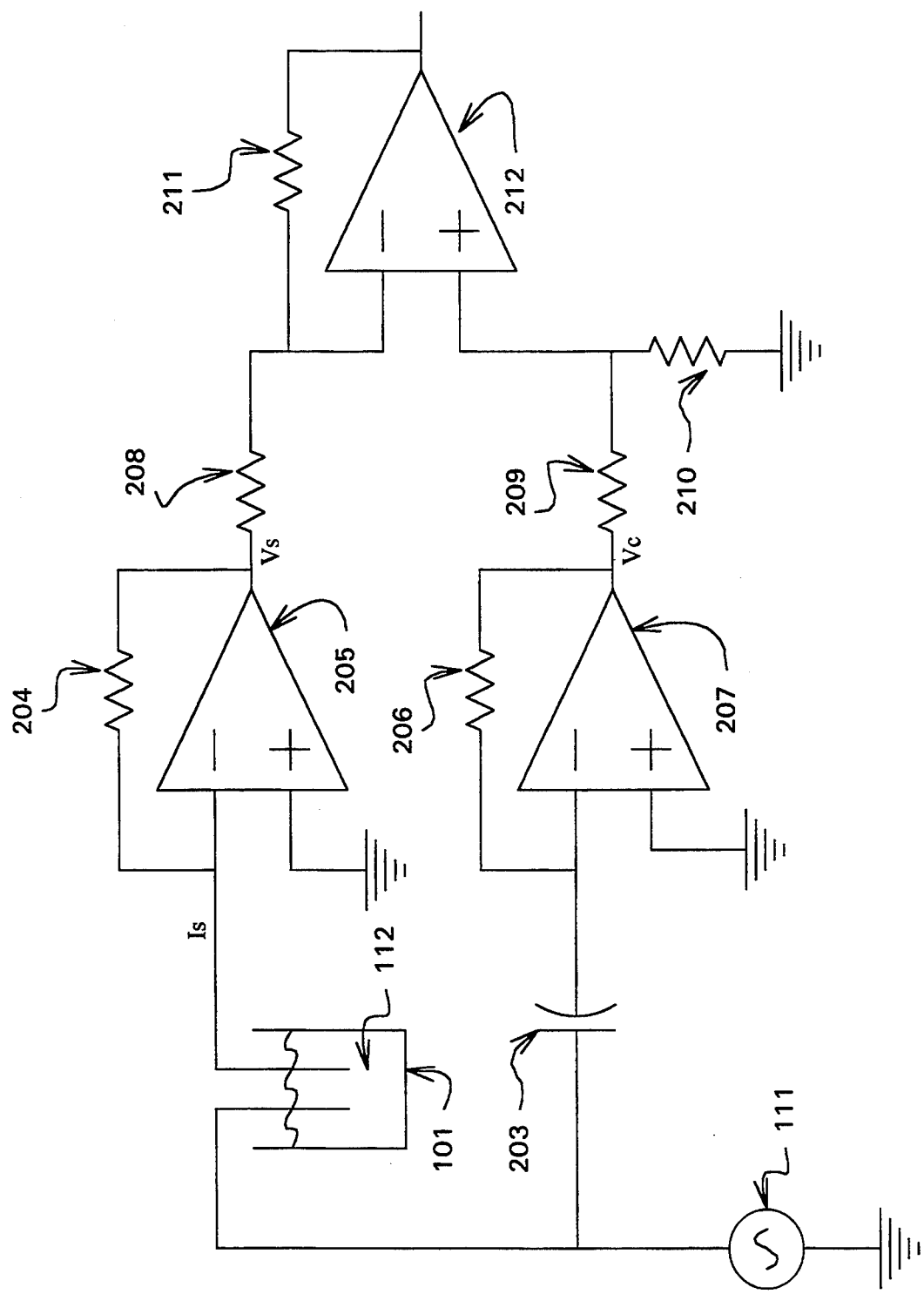
FIG. 2 is a schematic diagram of the amplifier of FIG. 1

Referring next to FIG. 2 where a preferred embodiment for amplifiers 105 or 107 of FIG. 1 is shown. Signal source 111, as stated above, supplies a low voltage AC signal to toner reservoir 101. Current $I_s$ flows through toner 112 and into OP-AMP 205. As configured in FIG. 2 OP-AMP 205, with the aid of resistor 204, converts current $I_s$ into a voltage $V_s$ such that $V_s$ is proportional to $I_s$. OP-AMP 207 produces a voltage $V_c$ that is proportional to the current through capacitor 203 where the value of capacitor 203 is approximately equal to the capacitance of toner 112. Finally, OP-AMP 212 subtracts $V_c$ from $V_s$ thereby attempting to minimize the effects of the capacitance of toner 112. The output of OP-AMP 212 is forwarded to a filter and AC to DC converter.

Figure 3:
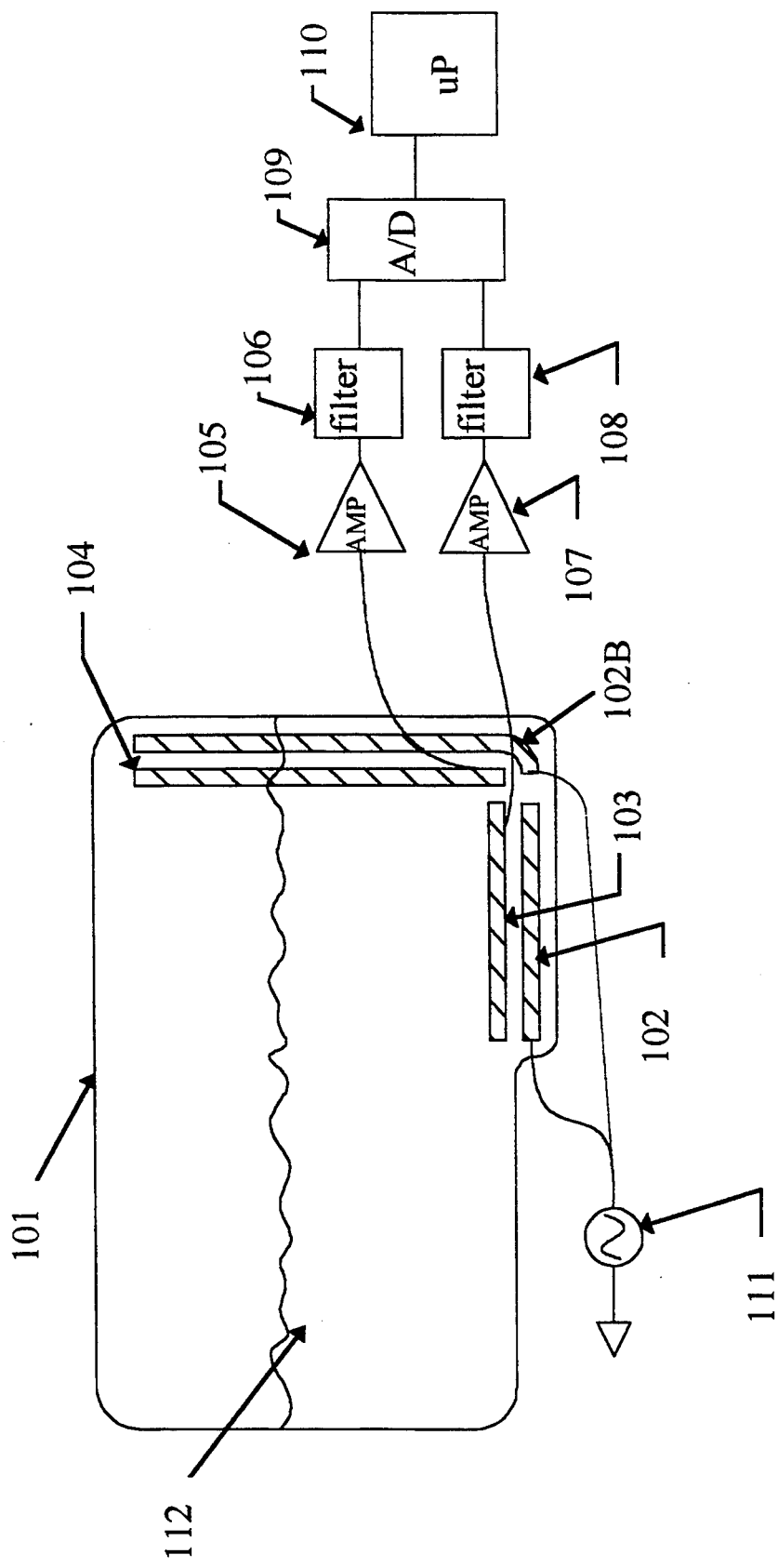
FIG. 3 is a simplified diagram of an alternative embodiment in accordance with the present invention.

Referring briefly to FIG. 3 where an alternative embodiment is shown. The primary difference between FIG. 1 and FIG. 3 can be seen by careful inspection of plate 102. In FIG. 1 plate 102 is a solid plate with an "L" shape, where as in FIG. 3 this plate has been broken into two plates 102 and 102B. Such an arrangement may be necessary to allow for easier manufacturing of the present invention.

As an alternative embodiment, toner volume measurement can simply indicate when the toner falls below a predetermined level. However, the cost to implement the indicator would not differ significantly from the continuous measurement method described above and less information is available to the user.

Analysis of the sensor plates is given below: For an RC Circuit, Current (I) is described as:

$$I = \frac{V_{max}}{Z_{RC}} \times \sin(2\pi ft + \phi_{RC}) \qquad \text{eq. 1}$$

or:

$$I_{rms} = \frac{V_{rms}}{Z_{RC}} \qquad \text{eq. 2}$$

where:

$$Z_{RC} = \frac{R}{\sqrt{1 + (\omega CR)^2}} \qquad \text{eq. 3}$$

Substituting equation 3 into equation 2 gives:

$$I_{rms} = \frac{V_{rms} \cdot \sqrt{1 + (\omega CR)^2}}{R} \qquad \text{eq. 4}$$

For exemplary purposes, using a plate size of 10 cm by 1 cm and a plate separation of 1.5 mm, the maximum and minimum resistance between the plates and the maximum and minimum capacitance between the plates can be calculated. For plate 103 the capacitance would not change however, it will be shown that the resistance will change in proportion to the toner concentration Plate 104's resistance will vary between the minimum value and infinity. One skilled in the art will know that each toner has different resistance values however, the numbers below are typical for black toner.

Given:
$A = 10 \cdot cm^2$     eq. 5
$d = 1.5 \cdot mm$     eq. 6
$\sigma_{toner2\%k} = 3970 \cdot 10^6 \cdot ohm\text{-}cm$     eq. 7
$\sigma_{toner6\%k} = 770 \cdot 10^6 \cdot ohm\text{-}cm$     eq. 8
$\epsilon_{air} = 8.9 \cdot 10^{-12} \cdot farad/meter$     eq. 9
$\epsilon_{toner} = 1.5 \cdot \epsilon_{air}$     eq. 10

$$R_{max} = \frac{\sigma_{toner2\%k} \cdot d}{A} \qquad \text{eq. 11}$$

$$R_{min} = \frac{\sigma_{toner6\%k} \cdot d}{A} \qquad \text{eq. 12}$$

-continued $$C_{air} = \frac{\epsilon_{air} \cdot A}{d} \qquad \text{eq. 13}$$

$$C_{toner} = \frac{\epsilon_{toner} \cdot A}{d} \qquad \text{eq. 14}$$

Then, for the present physical properties:

$R_{max} = 59.55 \cdot 10^6 \cdot ohm$     eq. 15

$R_{min} = 11.55 \cdot 10^6 \cdot ohm$     eq. 16

$C_{air} = 5.93 \cdot 10^{-12} \cdot farad$     eq. 17

$C_{toner} = 8.90 \cdot 10^{-12} \cdot farad$     eq. 18

From the above, the output current from plates 103 and 104 can be calculated. Let:

$V_{rms} = 6$ volts     eq. 19

$f = 60$ Hz     eq. 20

$\omega = 2\pi f$     eq. 21

Then for plate 103:

$$I_{max2} = \frac{6 \cdot \sqrt{1 + [(2\pi \cdot 60 \cdot (8.9 \cdot 10^{-12}) \cdot (12 \cdot 10^6)]^2}}{12 \cdot 10^6} = \qquad \text{eq. 22}$$
$$519.9 \cdot 10^{-9} \cdot amp$$

$$I_{min2} = \frac{6 \cdot \sqrt{1 + [(2\pi \cdot 60 \cdot (8.9 \cdot 10^{-12}) \cdot (60 \cdot 10^6)]^2}}{60 \cdot 10^6} = \qquad \text{eq. 23}$$
$$102.7 \cdot 10^{-9} \cdot amp$$

For plate 104:

$I_{max3} = I_{max2} = 519.9 \cdot 10^{-9} \cdot amp$     eq. 24

$I_{min3} = 2V\pi f C_{air} = 2 \cdot 6 \cdot \pi \cdot 60 \cdot 5.9 \cdot 10^{-12} 32$
$13.4 \cdot 10^{-9} \cdot amp$     eq. 25

Neglecting capacitance and repeating the calculations to find the capacitive effect.

$$I_{max2} = \frac{V}{R_{min}} = 519.5 \cdot 10^{-9} \cdot amp \qquad \text{eq. 26}$$

$$I_{min2} = \frac{V}{R_{max}} = 100.8 \cdot 10^{-9} \cdot amp \qquad \text{eq. 27}$$

Thus, comparing equations 26 and 27 with equations 15 and 16 shows that the effect of capacitance can be neglected as long as the frequency is low.

Given:

$$\lambda_c = \frac{1}{\sigma_c} \text{ which is toner conductivity.} \qquad \text{eq. 28}$$

Then for plate 103:

$$I_{plate2} = \frac{V}{R_2} = \frac{V \cdot A_2 \cdot \lambda_c}{d_2} \qquad \text{eq. 29}$$

Solving for conductivity:

$$\lambda_c = \frac{I_{plate2} \cdot d_2}{V \cdot A_2} \qquad \text{eq. 30}$$

where:

-continued $$\frac{d_2}{V \cdot A_2} = \text{constant} \quad \text{eq. 31}$$

So, $$\boxed{\lambda_c = K_2 \cdot I_{plate2}} \quad \text{eq. 32}$$

As equation 32 shows, toner Conductivity ($\lambda_c$) is directly proportional to the current ($I_{plate2}$) from plate 103.

For plate 104:

$$I_{plate3} = \frac{V}{R_3} = \frac{V \cdot A_3 \cdot \lambda_c}{d_3} \quad \text{eq. 33}$$

solving for whetted plate area:

$$A_3 = \frac{I_{plate3} \cdot d_3}{V \cdot \lambda_c} = \frac{I_{plate3} \cdot d_3 \cdot V \cdot A_2}{V \cdot I_{plate2} \cdot d_2} = \frac{I_{plate3} \cdot d_3 \cdot A_2}{I_{plate2} \cdot d_2} \quad \text{eq. 34}$$

where:

$$\frac{d_3 \cdot A_2}{d_2} = \text{constant} \quad \text{eq. 35}$$

So, $$\boxed{A_3 = K_3 \cdot \frac{I_{plate3}}{I_{plate2}}} \quad \text{eq. 36}$$

Therefore, toner level is directly proportional to the current from plate 104 divided by the current from plate 103.

The plate size and separation used in the above calculations are typical but, smaller or larger plates are feasible. Output current increases as the plates are placed closer together. However, toner needs to be flushed between the plates to prevent sediment from building up and to insure the concentration being measured is representative of the average concentration in the toner cartridge. An ideal location for the plates is at the pump inlet where the pump draws toner between the plates to provide flushing action.

The voltage and frequency at which the first plate is driven is also variable. Higher frequencies allow simpler filter designs but produce more capacitive effects and lower resistance values because charge mobility comes into effect. Measurements and calculations show that the output current becomes dominated by capacitive effects above about 500 Hz. Using a DC source, however, will cause toner particles to be electrically deposited on the electrodes. This plating effect may also be present at higher AC voltages. No toner plating has been observed at 6 volts rms and below.

Because the sensor output data is processed by microprocessor 110, configurations of toner cartridges that do not produce a toner level reduction directly proportional to toner volume can easily be compensated for by changing the microprocessor's software.

Although the preferred embodiment of the invention has been illustrated, and that form described, it is readily apparent to those skilled in the art that various modifications may be made therein without departing from the spirit of the invention or from the scope of the appended claims.

What is claimed is:

1. In a liquid electrophotographic printer, an apparatus for determining a concentration of solid in a liquid toner concentrate, said apparatus further measuring a volume of said liquid toner concentrate, said apparatus comprising of:

a first element having a first section and a second section, said first section being submerged in said liquid toner concentrate and said second section being submerged proportionally to an amount of said liquid toner concentrate;

a voltage source connected to said first element;

a second element in close proximity to said first section of said first element, said second element being submerged in said liquid toner concentrate;

a third element in close proximity to said second section of said first element, said third element being submerged proportionally to said amount of said liquid toner concentrate;

means for determining said concentration of solid being proportional to a first current flowing from said first element through said liquid toner concentrate to said second element; and means for determining said volume of said liquid toner concentrate being proportional to a second current flowing from said first element through said liquid toner concentrate to said third element divided by said first current.

2. An apparatus as claimed in claim 1 wherein said voltage source is an alternating voltage source.

3. An apparatus as claimed in claim 1 wherein:

said first current being processed by a first amplifier and a first filter to produce a first voltage;

said second current being processed by a second amplifier and a second filter to produce a second voltage; and said first voltage and said second voltage being processed by a processor, said processor multiplying said first voltage by a concentration factor to determine said concentration of solids, additionally, said processor multiplying said second voltage by a volume factor then dividing by said first voltage to determine said volume of said liquid toner concentrate.

4. In a liquid electrophotographic printer, an apparatus for determining a concentration of solid in a liquid toner concentrate, said apparatus further measuring a volume of said liquid toner concentrate, said apparatus comprising of:

a first element being submerged in said liquid toner concentrate;

a second element being submerged proportionally to an amount of said liquid toner concentrate;

a voltage source connected to said first element and said second element;

a third element in close proximity to said first element, said third element being submerged in said liquid toner concentrate;

a fourth element in close proximity to said second element, said fourth element being submerged proportionally to said amount of said liquid toner concentrate;

means for determining said concentration of solid being proportional to a first current flowing from said first element through said liquid toner concentrate to said third element; and means for determining said volume of said liquid toner concentrate being proportional to a second current flowing from said second element through said liquid toner concentrate to said fourth element divided by said first current.

5. An apparatus as claimed in claim 4 wherein said voltage source is an alternating current source.

6. An apparatus as claimed in claim 4 wherein:
said first current being processed by a first amplifier and a first filter to produce a first voltage;
said second current being processed by a second amplifier and a second filter to produce a second voltage; and
said first voltage and said second voltage being processed by a processor, said processor multiplying said first voltage by a concentration factor to determine said concentration of solids, additionally, said processor multiplying said second voltage by a volume factor then dividing by said first voltage to determine said volume of said liquid toner concentrate.

7. In a liquid electrophotographic printer, an apparatus for determining a concentration of solid in a liquid toner concentrate, said apparatus further measuring a volume of said liquid toner concentrate, said apparatus comprising of:
a container in which said liquid toner concentrate resides;
a first plate mounted at a bottom region inside said container whereby said first plate being submerged in said liquid toner concentrate;
a second plate mounted inside said container whereby said second plate being submerged proportionally to an amount of said liquid toner concentrate in said container;
a voltage source connected to said first plate and said second plate;
a third plate in close proximity and parallel to said first plate, said third plate being submerged in said liquid toner concentrate;
a fourth plate in close proximity and parallel to said second plate, said fourth plate being submerged proportionally to said amount of said liquid toner concentrate;
means for determining said concentration of solid being proportional to a first current flowing from said first plate through said liquid toner concentrate to said third plate; and
means for determining said volume of said liquid toner concentrate being proportional to a second current flowing from said second plate through said liquid toner concentrate to said fourth plate divided by said first current.

8. An apparatus as claimed in claim 7 wherein said first plate and said second plate being formed as a single unit and having an "L" shape.

* * * * *